United States Patent
Lake et al.

(10) Patent No.: US 9,084,975 B2
(45) Date of Patent: Jul. 21, 2015

(54) REAL-TIME ONLINE DETERMINATION OF CAUSTIC IN PROCESS SCRUBBERS USING NEAR INFRARED SPECTROSCOPY AND CHEMOMETRICS

(71) Applicant: SABIC Innovative Plastics IP B.V., Bergen op Zoom (NL)

(72) Inventors: Derek Lake, Evansville, IN (US); Yusuf Sulub, Newburg, IN (US); Zhensheng Ding, Mt. Vernon, IN (US)

(73) Assignee: SABIC Global Technologies B.V., Bergen op Zoom (NL)

(*) Notice: Subject to any disclaimer, the term of this patent is extended or adjusted under 35 U.S.C. 154(b) by 0 days.

(21) Appl. No.: 13/971,748

(22) Filed: Aug. 20, 2013

(65) Prior Publication Data
US 2014/0054464 A1    Feb. 27, 2014

Related U.S. Application Data

(60) Provisional application No. 61/691,214, filed on Aug. 20, 2012.

(51) Int. Cl.
| | | |
|---|---|---|
| *G01J 5/02* | (2006.01) | |
| *B01J 4/00* | (2006.01) | |
| *G01N 21/59* | (2006.01) | |
| *G01N 21/359* | (2014.01) | |
| *B01D 53/14* | (2006.01) | |

(52) U.S. Cl.
CPC ............ *B01J 4/008* (2013.01); *B01D 53/1412* (2013.01); *B01D 53/1456* (2013.01); *G01N 21/359* (2013.01); *G01N 21/59* (2013.01); *B01D 2251/304* (2013.01)

(58) Field of Classification Search
USPC ......... 250/341.1; 705/413; 354/437; 700/105
See application file for complete search history.

(56) References Cited

U.S. PATENT DOCUMENTS

| | | | |
|---|---|---|---|
| 4,563,427 A | 1/1986 | Weiss et al. | |
| 5,597,445 A * | 1/1997 | Westerberg | 162/29 |
| 6,235,934 B1 * | 5/2001 | Caringi et al. | 564/241 |
| 6,359,102 B1 * | 3/2002 | Kemnitzer et al. | 528/179 |
| 6,641,638 B1 * | 11/2003 | Lueck et al. | 71/59 |
| 7,771,654 B1 * | 8/2010 | Moore et al. | 422/62 |
| 2004/0020278 A1 | 2/2004 | McGarvey et al. | |

(Continued)

OTHER PUBLICATIONS

"ABB Analytical—PIR3502 Multiwave process photometer: Caustic monitoring in acid gas scrubbers," ABB Analytical, http://www05.abb.com/global/scot/scot205.nsf/veritydisplay/d94b6c8560672d5c852578fe004a7855/$file/a_n%20pir3502%20caustic%20monitoring%20in%20acid%20gas-%20scrubbers%208162011.pdf (last visited Nov. 22, 2013).

(Continued)

*Primary Examiner* — David J Makiya
*Assistant Examiner* — Taeho Jo
(74) *Attorney, Agent, or Firm* — Baker & Hostetler LLP

(57) ABSTRACT

Disclosed herein are processes, apparatuses, and systems for monitoring and/or controlling caustic concentrations in caustic scrubbers. In various aspects, the processes, apparatuses, and systems comprise a real-time online method for measuring the concentration of caustic in process scrubbers wherein a probe is coupled to a spectrometer; collecting absorption data with wavelength range from about 1000 to about 2000 nm. In a further aspect, this technique tracks the use and recharge of caustic in process scrubbers. This abstract is intended as a scanning tool for purposes of searching in the particular art and is not intended to be limiting of the present invention.

32 Claims, 7 Drawing Sheets

(56) References Cited

U.S. PATENT DOCUMENTS

| | | | |
|---|---|---|---|
| 2005/0115674 A1* | 6/2005 | Taguchi et al. | 156/345.29 |
| 2006/0249464 A1* | 11/2006 | Conger et al. | 210/760 |
| 2007/0099038 A1* | 5/2007 | Galloway | 429/17 |
| 2009/0292098 A1* | 11/2009 | Wagner et al. | 528/48 |
| 2009/0320683 A1* | 12/2009 | Hintz | 95/185 |
| 2010/0159606 A1 | 6/2010 | Nakaminami et al. | |
| 2010/0228688 A1* | 9/2010 | Little et al. | 705/413 |
| 2010/0239467 A1* | 9/2010 | Constantz et al. | 422/168 |
| 2011/0097810 A1* | 4/2011 | Soleta et al. | 436/104 |
| 2011/0217226 A1* | 9/2011 | Mosa et al. | 423/418.2 |
| 2011/0262343 A1* | 10/2011 | Hojjatie et al. | 423/514 |
| 2012/0064466 A1* | 3/2012 | Roth et al. | 431/159 |
| 2012/0178864 A1 | 7/2012 | Keiser et al. | |
| 2012/0298592 A1* | 11/2012 | Boal et al. | 210/748.15 |
| 2013/0053487 A1* | 2/2013 | Gallucci et al. | 524/127 |

OTHER PUBLICATIONS

"Application note—Caustic in water with a ClearView (R) filter photometer system," Guided Wave Inc.

"Application note—On-line monitoring of caustic aand carbonate with a Chemview (R) photometer," Guided Wave Inc.

"Application Report #Chem30: Quantitative Analysis of Sodium Hydroxide in Chlorine Scrubbing Solutions." Brimrose. Report requested from: http://www.brimrose.com/products/nir_mir_spectrometers/process_applications/chemical30.html.

Cardis TM. "Online NIR photometer applications," JPAC, http://www.infoscience.com/JPAC/ManScDB/JPACDBEntries/1015015902.pdf (last visited Nov. 22, 2013).

"Near infrared analysis applications," Sensevolution 2013, http://sensevolution.baggi.com/spectroscopy-analysis-applications/11-near-infrared-analysis-applications.html (last visited Nov. 22, 2013).

"O-SST Probe and Fiber Optic Cable Installation and Maintenance Manual," Guided Wave Inc.

International Search Report issued Oct. 29, 2013 by the International Searching Authority for International Patent Application PCT/US2013/055849 filed Aug. 20, 2013 which published as WO 2014/031678 on Feb. 27, 2014 (Inventor—Derek Lake// Applicant—SABIC Innovative Plastics IP, B.V.) (5 pages).

* cited by examiner

REAL-TIME ONLINE DETERMINATION OF CAUSTIC IN PROCESS SCRUBBERS USING NEAR INFRARED SPECTROSCOPY AND CHEMOMETRICS

CROSS-REFERENCE TO RELATED APPLICATIONS

This Application claims the benefit of U.S. Provisional Application No. 61/691,214, filed on Aug. 20, 2012, which is incorporated herein by reference in its entirety.

FIELD OF INVENTION

The present invention relates to caustic scrubbers. More specifically, the invention relates to processes, apparatuses, and systems for monitoring and/or controlling caustic concentrations in caustic scrubbers.

BACKGROUND

Process scrubbers are prevalent in chemical industry. In polycarbonate (PC) production, caustic scrubbers are frequently used to remove acidic gases by converting them to salt, water, and carbon dioxide. This is typically done by mixing the acidic effluents from the reactors with caustic in a column via a counter flow system. As the acidic effluents react with the caustic, this operation depletes the caustic strength. To maintain adequate levels of caustic, the concentration of caustic is normally monitored through a manual sampling, and the caustic concentration is determined with a manual acid-base titration. Such caustic strength analysis is typically done on a regular periodicity throughout the day. Depending on the titration results, the caustic concentration can be adjusted by adding fresh caustic solution to the scrubber. A long time period between the manual caustic measurements can result in inefficient operation of the scrubbers and possible process safety issues. Thus, there is a need for a real-time online solution to ensure safe operation and efficient use of caustic. This need and other needs are satisfied by the disclosed invention.

SUMMARY OF THE INVENTION

As described in more detail herein, the present invention provides processes, apparatuses, and systems for monitoring and/or controlling caustic concentrations in caustic scrubbers.

In one aspect, the invention relates to a monitoring process comprising the steps of: providing a spectroscopy probe coupled to a caustic scrubber; and measuring the near-infrared absorbance in the scrubber.

In a further aspect, the invention relates to a caustic scrubber comprising a near-infrared spectroscopy probe coupled thereto.

In a further aspect, the invention relates to a polycarbonate production system comprising the disclosed caustic scrubber and/or the disclosed monitoring process.

BRIEF DESCRIPTION OF THE FIGURES

The accompanying figures, which are incorporated in and constitute a part of this specification, illustrate several aspects and together with the description serve to explain the principles of the invention.

Figure 1A:
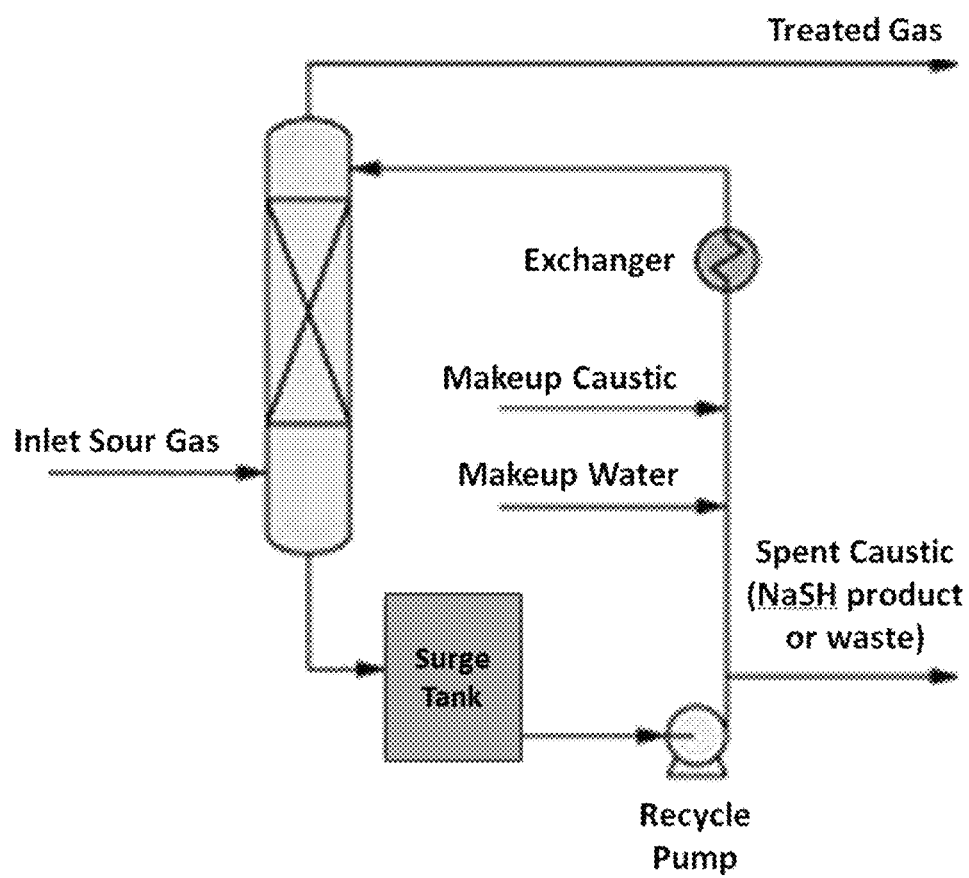
FIG. 1A is a schematic of a caustic scrubber.
Figure 1B:
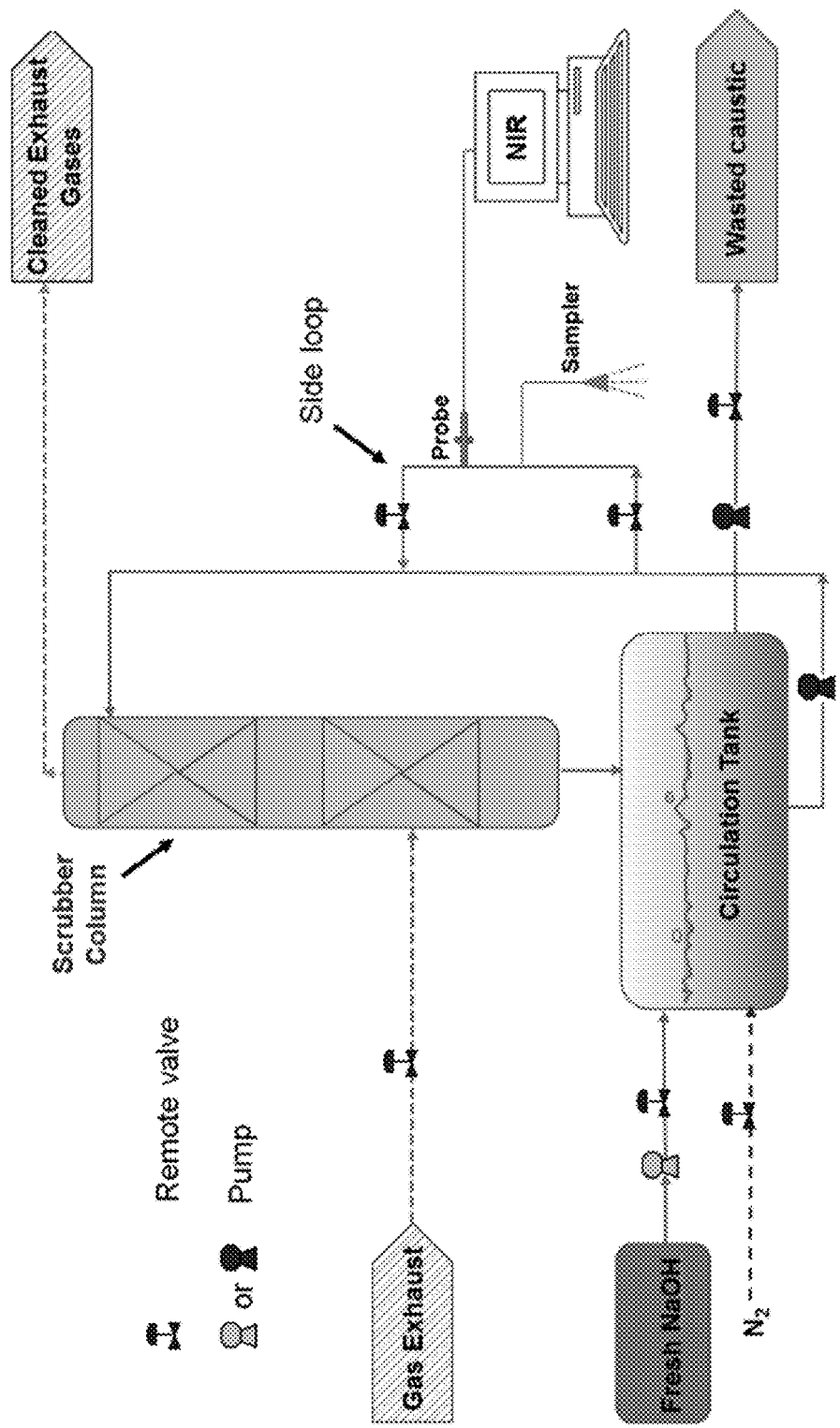
FIG. 1B is a schematic of a caustic scrubber.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a ketone" includes mixtures of two or more ketones.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or can not be substituted and that the description includes both substituted and unsubstituted alkyl groups.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included. For example if a particular element or component in a composition or article is said to have 8% weight, it is understood that this percentage is relation to a total compositional percentage of 100%.

As used herein "means for determining caustic concentration" refers to the use of a chemometric model to predict caustic strength of the analyte stream from the NIR spectra data. Briefly, NIR spectra are collected on solutions for which the caustic strength has been determined by an off-line titration method. This caustic strength data is paired up with its corresponding NIR spectrum and used together in constructing a chemometric model. Numerous spectra with corresponding caustic concentration data are used in constructing the model. In predicting the caustic strength, the sample NIR spectra are fed into the model. The model then predicts the concentration of caustic based upon that NIR spectrum.

As used herein "means to automatically introduce caustic into the scrubber to maintain a concentration range" refers to the interface of the means for determining caustic concentration with a plant control system wherein when the caustic concentration in the analyte stream falls below the lower control limit as determined using the means for determining caustic concentration, then a signal is conveyed to the plant control system to dispense into the scrubber stream fresh caustic solution. The amount of fresh caustic solution to dispense, as conveyed to the plant control system, is related to the difference between the caustic strength as determined by the means for determining caustic concentration and the lower control limit.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Near-Infrared (NIR) Spectroscopy

Near-infrared (NIR) is a widely used analytical measurement tool in chemical, pharmaceutical, petroleum, and agricultural industries. The technique requires little or no sample preparation and is nondestructive, reagentless, simple, and fast. In addition, NIR spectroscopy exhibits the capability to extract quantitative information of several species within a sample from a measured spectrum thereby making this approach ideal for multicomponent determination of complex matrixes.

In one aspect, the present invention provides a method to reduce analysis cycle time, improve the safety of scrubber operations, and allows for the efficient use of cause via an online spectroscopic technique as disclosed herein.

Near infrared (NIR) spectroscopy covering the 1000-2500 nm (10000-4000 $cm^{-1}$) wavelength region is proposed for direct measurement of the caustic scrubber stream. Briefly, a probe is inserted into the process stream, the probe is connected to a spectrometer via fiber optic cables, and NIR spectra acquired from the probe. Various probes suitable for use in the present invention are commercially available, including, for example, the Guided Wave O-Ring Single Sided Transmission (O-SST) probe. Suitable NIR spectrophotometers for use in the methods of the present invention, including, but not limited to, Bruker Matrix-F FT-NIR spectrometer, Thermo Antaris MX FT-NIR spectrometer, ABB FTPA 2000 FT-NIR spectrometer, and Foss NIR XDS Process Analyzer. The NIR methods of the present invention is advantageous compared to prior art methods because it is non-destructive, requires no sample collection or preparation, and provides real-time measurements.

The present NIR spectroscopic method is calibrated using known standard caustic concentrations. The known caustic concentrations and corresponding NIR spectra are coupled and a model was developed that relates the spectra to the caustic concentration. The model is a chemometric based method known as partial least squares (PLS) regression and allows determination of caustic concentration in about 60 sec or less.

The chemometric based PLS calibration uses a range of wavelengths in conjunction with myriad spectral pretreatment algorithms to construct a more accurate and reproducible model. The use of wavelength range and spectral pretreatment minimizes the influence of other chemical species present in matrix (such as carbonates, salts, and methylene chloride) and process factors (temperature and flow rate).

Real-time online measurements of caustic in process scrubber stream makes the caustic analysis much safer compared to prior art described earlier and enables significant economic benefit by efficiently utilizing the caustic in the process scrubber. This is realized especially if the data is used immediately in a distributed control system whereby the digital data from the NIR model is used to control the caustic level in the circulation tank.

Monitoring Processes

In one aspect, the invention relates to a monitoring process comprising the steps of: providing a spectroscopy probe coupled to a caustic scrubber; and measuring the near-infrared absorbance in the scrubber. In a further aspect, coupling is via direct contact. In a further aspect, coupling is via fiber optic.

In a further aspect, a NIR transmission probe is inserted in a side loop of the main scrubber column. In a still further aspect, online NIR spectra are acquired in real-time. In a yet further aspect, the caustic scrubber is part of a polycarbonate production system. In an even further aspect, the process further comprises the step of determining caustic concentration in the scrubber from the measured absorbance. In a still further aspect, the determining step is a chemometric-based method using partial least squares (PLS) regression which correlates the NIR spectra to reference titration values.

In a further aspect, the caustic scrubber is part of a polycarbonate production system. In a still further aspect, the process further comprises the step of determining caustic concentration in the scrubber from the measured absorbance. In a yet further aspect, the determining step is a chemometric-based method with spectral averaging over a time period of from about 15 seconds to about 5 minutes.

In a further aspect, caustic is sodium hydroxide. Suitable basic material includes alkali hydroxide, ammonia or ammonium hydroxide. In a further aspect, both caustic and sodium carbonate are measured.

In a further aspect, the method further comprises the step of introducing caustic into the scrubber to maintain a concentration range of from about 2 wt % to about 25 wt % caustic. In a yet further aspect, the concentration range is from about 5% to about 15%. In a still further aspect, the concentration range is from about 6% to about 8%. In a further aspect, the caustic is introduced automatically in response to the measured absorbance to maintain the concentration range.

In a further aspect, the absorbance is measured from about 1000 nm to about 2000 nm. In a further aspect, the absorbance is measured from about 1700 nm to about 2300 nm.

In a further aspect, the Reynolds Number of the fluid flow in the scrubber is less than 1500. In a further aspect, the Reynolds Number of the fluid flow in the scrubber is greater than 4000.

In a further aspect, the invention relates to a process for monitoring and controlling caustic concentration in a caustic scrubber of a polycarbonate production system, the process comprising the steps of: coupling, via fiber optic, to a caustic scrubber; measuring the near-infrared absorbance from about 1000 nm to about 2000 nm in the scrubber; determining caustic concentration in the scrubber from the measured NIR spectra via a chemometric-based method using partial least squares (PLS) regression; and introducing, in response to the measured caustic content by NIR, caustic into the scrubber to maintain a concentration range of from about 2 wt % to about 25 wt %.

Caustic Scrubbers

Waste streams produced in various chemical processes can contain acidic effluent. It is desirable to lower the level of acidity before it is introduced into the atmosphere in order to minimize the release of pollutants to the atmosphere.

In various aspects, the caustic is introduced in response to the measured absorbance to maintain the concentration range. In a further aspect, the caustic is introduced in response to the measured absorbance in accordance with a pre-determined set point value. In a still further aspect, the caustic is introduced automatically into the scrubber. In a yet further aspect, the automatic introduction of caustic is in accordance with a pre-programmed algorithm.

In one aspect, the invention relates to a caustic scrubber comprising a near-infrared spectroscopy probe coupled thereto. In a further aspect, the probe is coupled to the scrubber via direct contact. In a further aspect, the probe is coupled to the scrubber via fiber optic. In a still further aspect, the method further comprises means to automatically introduce caustic into the scrubber. In a further aspect, the caustic scrubber is part of a polycarbonate production system.

In a further aspect, the method further comprises the step of introducing caustic into the scrubber to maintain a concentration range of from about 2 wt % to about 25 wt % caustic. In a still further aspect, the concentration range is from about 2 wt % to about 20 wt %. In a yet further aspect, the concentration range is from about 2 wt % to about 15 wt %. In an further aspect, the concentration range is from about 2 wt % to about 14 wt %. In a still further aspect, the concentration range is from about 2 wt % to about 12 wt %. In a yet further aspect, the concentration range is from about 2 wt % to about 10 wt %. In an even further aspect, the concentration range is from about 2 wt % to about 8 wt %. In a still further aspect, the concentration range is from about 2 wt % to about 6 wt %.

In a further aspect, the method further comprises the step of introducing caustic into the scrubber to maintain a concentration range of from about 5 wt % to about 15 wt %. In a still further aspect, the concentration range is from about 5 wt % to about 14 wt %. In a yet further aspect, the concentration range is from about 5 wt % to about 13 wt %. In an even further aspect, the concentration range is from about 5 wt % to about 12 wt %. In a still further aspect, the concentration range is from about 5 wt % to about 11 wt %. In a yet further aspect, the concentration range is from about 5 wt % to about 10 wt %. In an even further aspect, the concentration range is from about 5 wt % to about 9 wt %. In a still further aspect, the concentration range is from about 5 wt % to about 8 wt %.

In a further aspect, the method further comprises the step of introducing caustic into the scrubber to maintain a concentration range of from about 6 wt % to about 24 wt %. In a still further aspect, the concentration range is from about 6 wt % to about 22 wt %. In a yet further aspect, the concentration range is from about 6 wt % to about 20 wt %. In an even further aspect, the concentration range is from about 6 wt % to about 18 wt %. In a still further aspect, the concentration range is from about 6 wt % to about 16 wt %. In a yet further aspect, the concentration range is from about 6 wt % to about 14 wt %. In an even further aspect, the concentration range is from about 6 wt % to about 12 wt %. In a still further aspect, the concentration range is from about 6 wt % to about 10 wt %. In a yet further aspect, the concentration range is from about 6 wt % to about 8 wt %.

In a further aspect, the method further comprises the step of introducing caustic into the scrubber to maintain a concentration range of from about 50% to about 100% of the maximum upper level of caustic. In a still further aspect, the method further comprises the step of introducing caustic into the scrubber to maintain a concentration range of from about 60% to about 100% of the maximum upper level of caustic. In a yet further aspect, the method further comprises the step of introducing caustic into the scrubber to maintain a concentration range of from about 70% to about 100% of the maximum upper level of caustic. In an even further aspect, the method further comprises the step of introducing caustic into the scrubber to maintain a concentration range of from about 50% to about 75% of the maximum upper level of caustic.

In a further aspect, the caustic is introduced automatically in response to the measured absorbance to maintain the concentration range.

In a further aspect, the invention relates to a caustic control system in a polycarbonate production system, the scrubber comprising: a caustic scrubber; a spectroscopy probe coupled to the scrubber via fiber optic, wherein the probe is capable of measuring the near-infrared absorbance in the scrubber; means for determining caustic concentration in the scrubber from the measured absorbance; and means to automatically introduce caustic into the scrubber to maintain a concentration range of from about 2% to about 25%. In a still further aspect, the concentration range is from about 5 wt % to about 15 wt %.

In a further aspect, the caustic control system further comprises a signal interface from means to automatically introduce caustic into the scrubber comprises to the means for determining caustic concentration in the scrubber to the means to automatically introduce caustic into the scrubber. In a still further aspect, the means to automatically introduce caustic into the scrubber comprises a programmed logic controller/distributed control system ("PLC/DCS"), wherein an output signal from the PLC/DCS interfaces with a means to introduce caustic into the scrubber, e.g. an electromechanical valve.

Alternatively, the addition to fresh caustic solution may be carried out entirely by manual operation. That is, based on information provided by the means for determining caustic concentration, a human operator can add fresh caustic solution to the scrubber by opening a valve that allows fresh caustic to flow into the scrubber. The amount of fresh caustic solution added being determined by the difference between the caustic concentration as determined by the means for determining caustic concentration and the lower control limit.

Polycarbonate Production Systems

In one aspect, the invention relates to a polycarbonate production system comprising the disclosed caustic scrubbers. In a further aspect, the polycarbonate production system is configured to perform the disclosed processes. In a further aspect, the polycarbonate production system comprises the disclosed caustic scrubbers and configured to perform the disclosed processes. In a further aspect, the polycarbonate production system comprises the disclosed caustic control systems. In a further aspect, the polycarbonate production system is configured to perform the disclosed processes. In a further aspect, the polycarbonate production system comprises the disclosed caustic control systems and configured to perform the disclosed processes.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

EXAMPLES

The following examples are put forth so as to provide those of ordinary skill in the art with a complete disclosure and description of how the methods, devices, and systems disclosed and claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in degrees Celsius (° C.) or is at ambient temperature, and pressure is at or near atmospheric.

Example 1

A sample was obtained from the side loop of a caustic scrubber and analyzed by titration. One gram of the sample was weighed into a 120 ml sample cup, and then 50 ml of distilled water was added. The sample was then titrated with 1 N hydrochloric acid (HCl) until the end point was reached. Sampling and measurements were done about every 8 hours. This method provides for discrete sampling without any additional information on caustic concentration in scrubbers between the 8 hr sampling intervals. The total analysis time for titration is about 10 minutes.

At the same instant titration sample was being collected, three replicate NIR spectral measurements were acquired via the probe in the side loop. These spectra were acquired before and after the sampling for titration measurement by manually requesting a scan so that a comparison of the caustic by titration and caustic by NIR could be realized. The NIR spectrometer used in this example was a Guided Wave Process 412 NIR spectrometer (Rancho Cordova, Calif.) coupled to an O-ring single sided (O-SST) transmission probe via fiber optics. The pathlength of the transmission probe was 2 mm and the instrument's resolution was 1 nm. The comparative study was carried out for two months. Replicate NIR measurements acquired were averaged for each time point. In total there were 93 comparative data points.

In anticipation of analyzing caustic scrubber samples in the process stream, the Guided Wave NIR spectrometer was first calibrated on a set of standards with caustic concentrations that spanned the entire target range to be measured. The calibration curve obtained was then stored in the computer controlling the spectrometer.

The acquired NIR spectra were then subjected to the chemometric based PLS regression model for caustic which outputs the caustic concentration. Direct NIR measurement followed by subsequent computation of caustic concentration was done in process stream is non-destructive, without sample preparation and use of reagents. The NIR spectral scan ranges from 1000-2100 nm. The spectral region from 1000-1800 nm is used for the PLS regression model.

Figure 2:
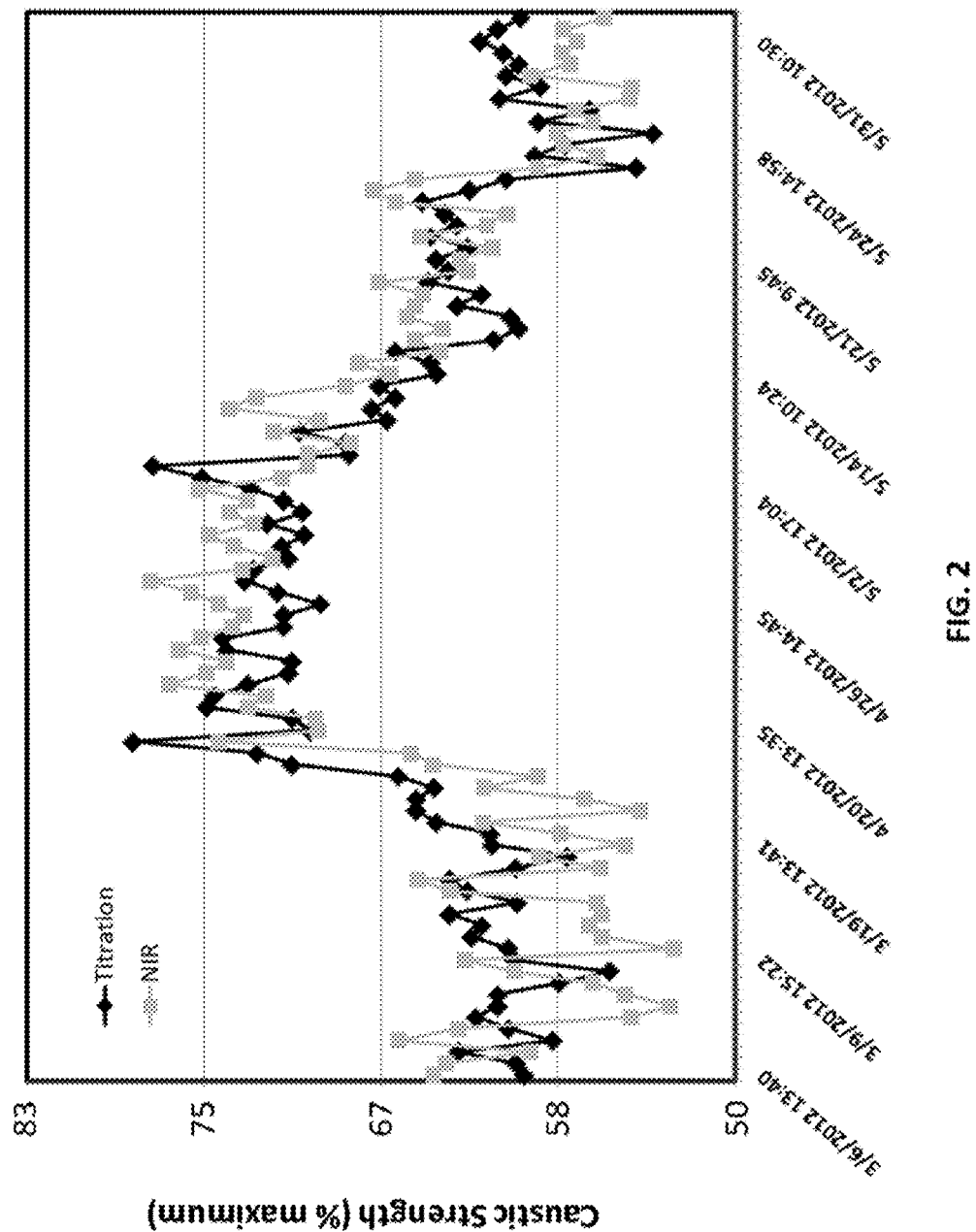
FIG. 2 shows representative data comparing real-time near infrared (NIR) and titration methods on caustic scrubber samples.

The results for 93 comparative samples are shown in FIG. 2. Visual inspection clearly shows that the two measurement systems are similar. Statistical comparison based on paired t-test revealed the difference between the two measurement systems was not significant (p=0.38). However, the total analysis time for the online NIR is less than 1 minute making it suitable for real-time analysis and process monitoring.

Example 2

The same spectrometer and probe configuration described in Example 1 were used in this example. The transmission probe was inserted into the process stream via the side loop and measured the NIR signal of the caustic flowing through the side loop. The same chemometric based PLS regression caustic model utilizing 1000-1800 nm was used to compute the caustic concentration in real-time. Data acquisition and subsequent caustic concentration output was programmed for once every 5 minutes for 15 days, resulting in a the collection and analysis of 4,320 NIR spectra.

Figure 3A:
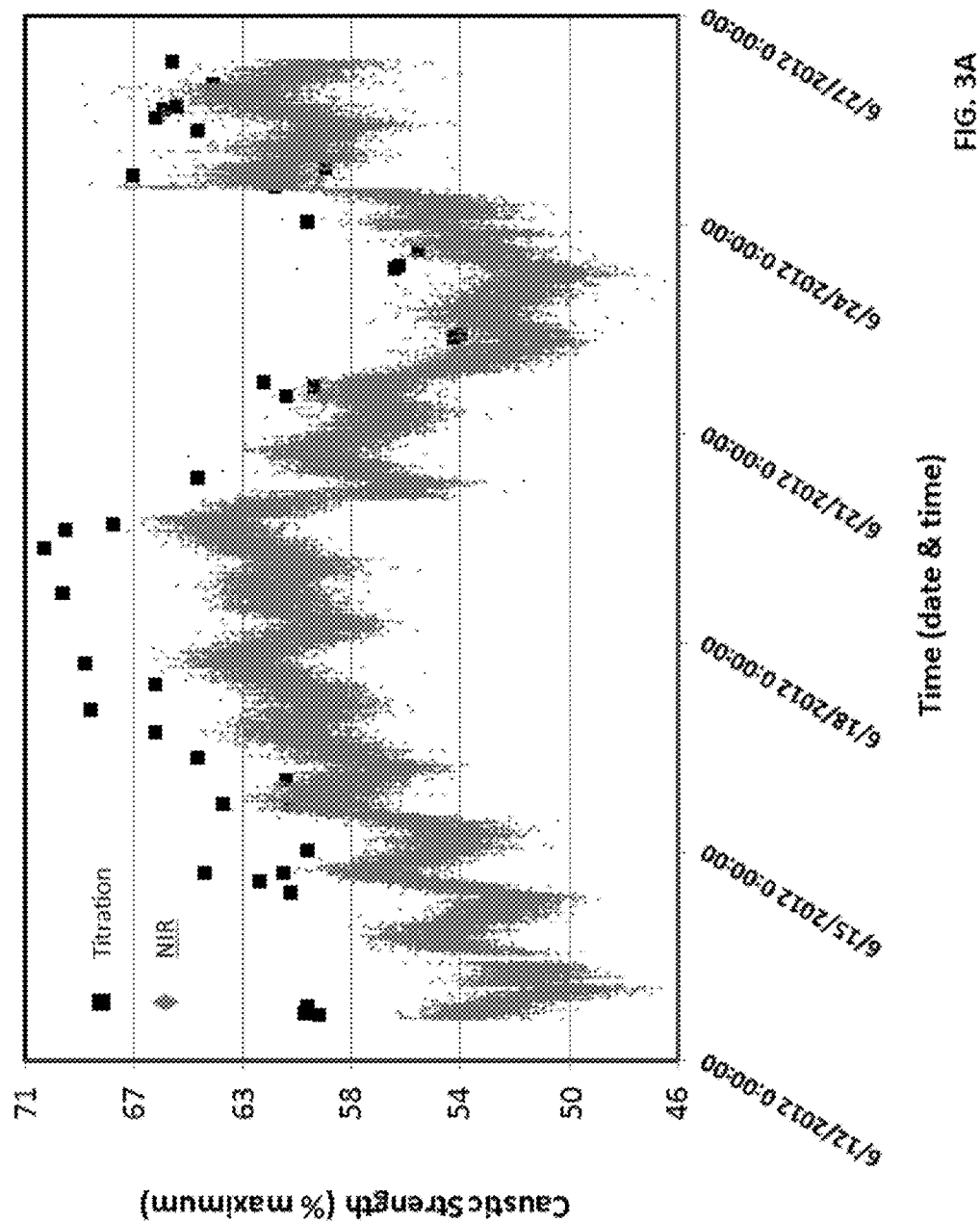
FIG. 3A shows representative data comparing online real-time near infrared (NIR) and titration caustic values.
Figure 3B:
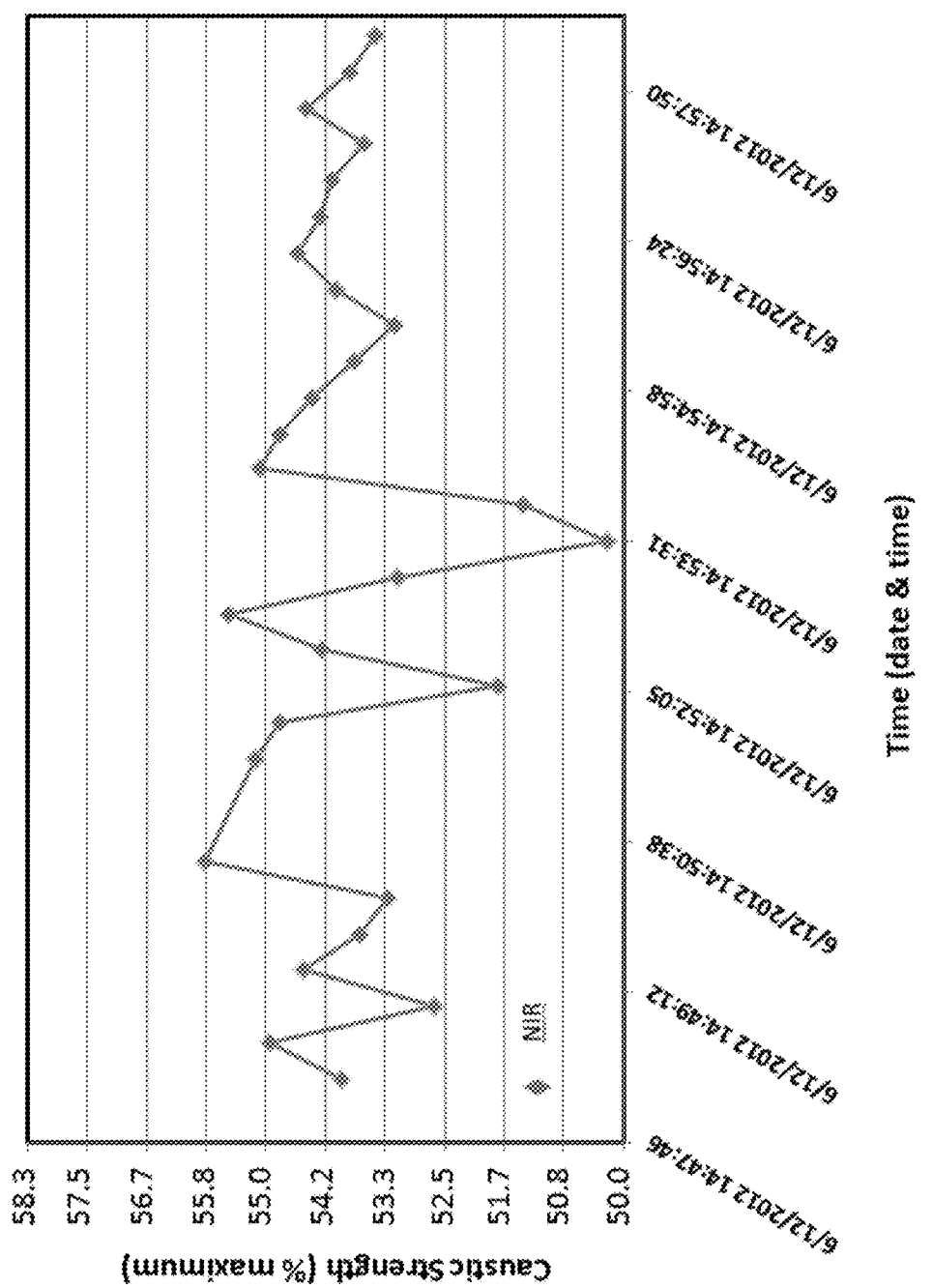
FIG. 3B shows a representative dataset within the 14 day period showing the frequency of sampling for the online real-time NIR method.

The results for the exemplary real-time online NIR analysis (gray diamond symbols in FIGS. 3A-3B) and comparison to titration results (black square symbols in FIG. 3A) are displayed in FIGS. 3A-3B. Visual inspection clearly shows the two measurement systems are comparable. The results in this example show that the caustic level can be controlled in real-time with an improved cycle time and safer operation of the caustic scrubbers.

Example 3

The same spectrometer and probe configuration as described in Example 1 were used in this example. The transmission probe was inserted into the process stream via the side loop and measured the NIR signal of the caustic flowing through the side loop. The same chemometric based PLS regression caustic model utilizing 1000-1800 nm was used to compute the caustic concentration in real-time. Data acquisition and subsequent caustic concentration output was programmed for once every 1 minute, corresponding to 1,440 spectra collected and analyzed.

Figure 4:
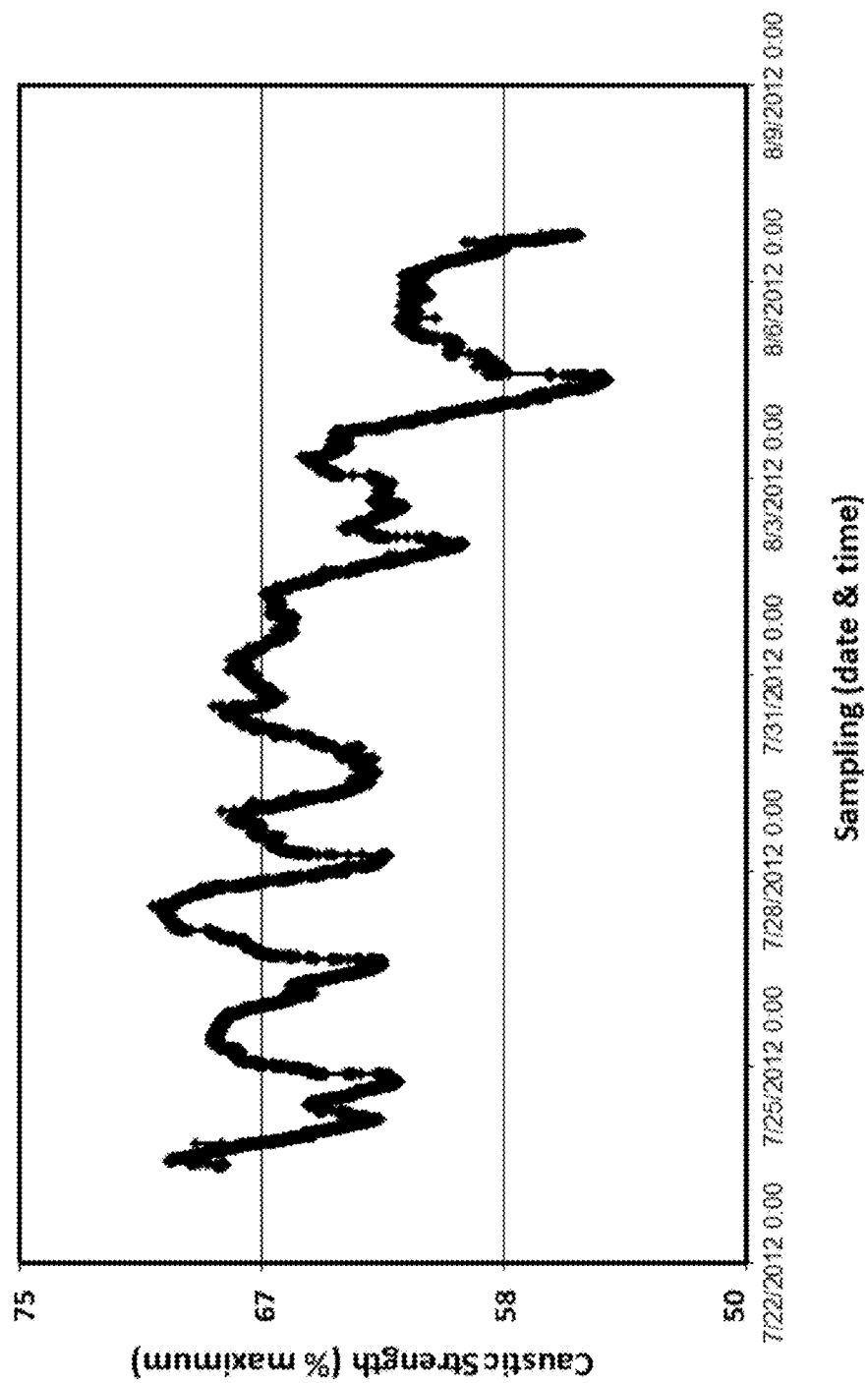
FIG. 4 shows representative data for real-time online near infrared (NIR) caustic monitoring.
Figure 5:
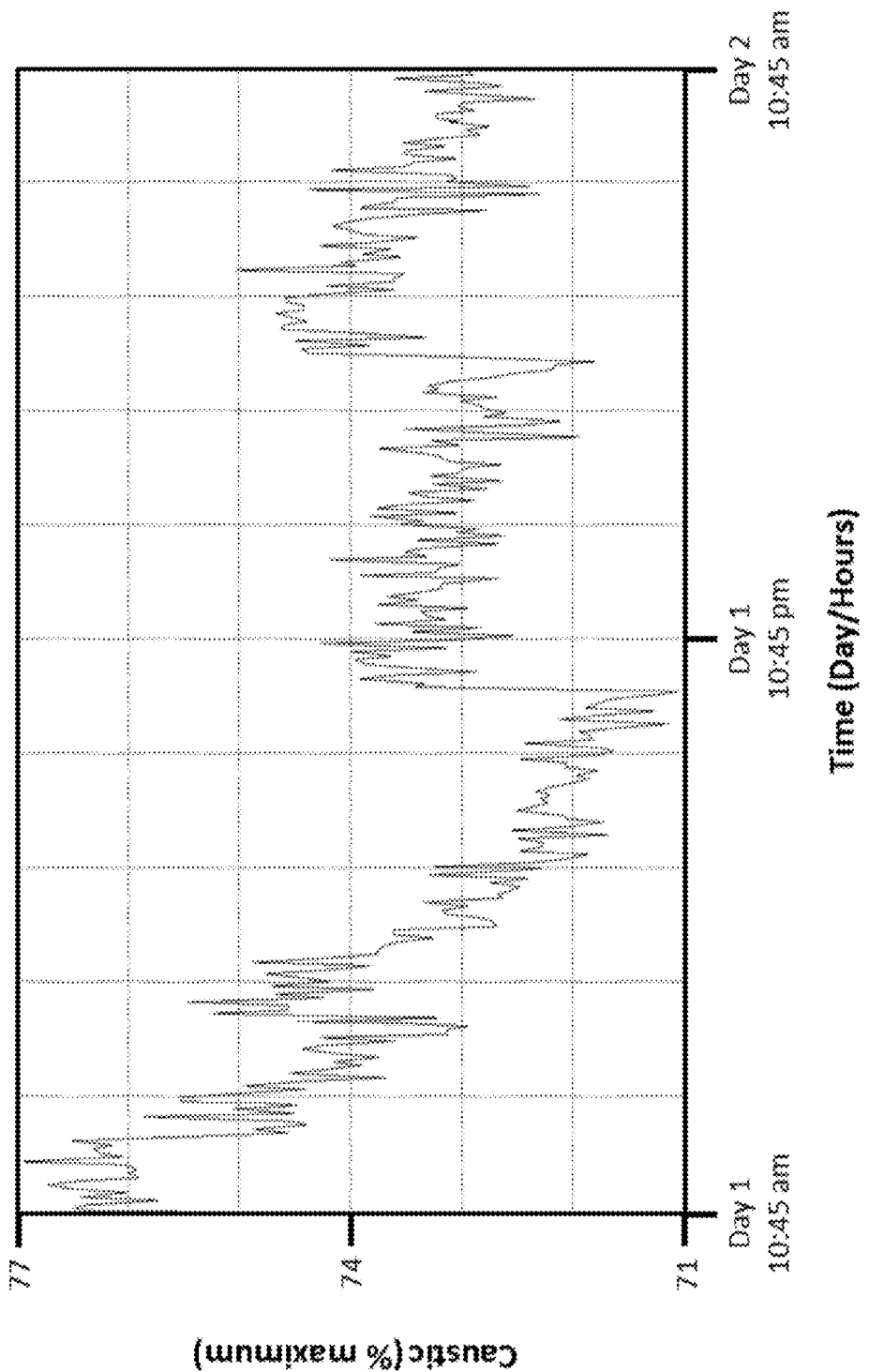
FIG. 5 shows representative data for the perturbation of the real-time online near-infrared (NIR) caustic concentration within 24 hour period.

Acidic gases emanating from the resin reactor and centrifuge feed tank react with caustic in the caustic column and are neutralized. The immediate consequence of this is the concentration of caustic is reduced and eventually the neutralized caustic is pumped to the waste tank. When the caustic level in the circulation tank falls below 70%, this automatically triggers the need to pump fresh caustic such that the level is brought up to 75%. This subsequently registers as an increase in caustic concentration. The data shown in FIG. 4 represent the caustic concentration over several weeks. FIG. 5 shows data pertaining to the perturbation of the caustic concentration within 24 hours.

The decline in the caustic concentration corresponds to neutralization of the caustic by acidic gases while the increase in the caustic concentration is due to the recharging of the circulation tank. These data clearly show the benefits of the present methods comprising real-time online monitoring of caustic levels in process scrubbers. This phenomenon was not evidenced when caustic monitoring and control was linked to a discrete measurement scheme of titration.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A monitoring process comprising the steps of:
   (a) providing a spectroscopy probe coupled to a caustic scrubber;
   (b) measuring the near-infrared absorbance in the scrubber; and
   (c) introducing caustic into the scrubber to maintain a concentration range of from about 5% to about 15%, wherein the caustic is introduced in response to the measured absorbance in accordance with a pre-determined set point value.

2. The process of claim 1, wherein coupling is via direct contact.

3. The process of claim 1, wherein coupling is via fiber optic.

4. The process of claim 1, wherein the probe is a NIR transmission probe.

5. The process of claim 1, wherein caustic is sodium hydroxide.

6. The process of claim 1, further comprising the step of determining caustic concentration in the scrubber from the measured absorbance.

7. The process of claim 6, wherein the determining step is a chemometric-based method with spectral averaging over a time period of from about 15 seconds to about 5 minutes.

8. The process of claim 1, wherein the caustic scrubber is part of a polycarbonate production system.

9. The process of claim 1, wherein the concentration range is from about 6% to about 8%.

10. The process as in any of claim 1 or 9, wherein the caustic is introduced automatically into the scrubber.

11. The process of claim 10, wherein the automatic introduction of caustic is in accordance with a pre-programmed algorithm.

12. The process of claim 1, wherein the absorbance is measured from about 1000 nm to about 2000 nm.

13. The process of claim 1, wherein the Reynolds Number of the fluid flow in the scrubber is less than 1500.

14. The process of claim 1, wherein the Reynolds Number of the fluid flow in the scrubber is greater than 4000.

15. A polycarbonate production system configured to perform the process of claim 1.

16. The process of claim 1, further comprising performing the process on a polycarbonate production system.

17. A process for monitoring and controlling caustic concentration in a caustic scrubber of a polycarbonate production system, the process comprising the steps of:
   (a) coupling, via fiber optic, a NIR transmission probe to a caustic scrubber;
   (b) measuring the near-infrared absorbance from about 1000 nm to about 2000 nm in the scrubber;
   (c) determining caustic concentration in the scrubber from the measured absorbance via a chemometric-based method; and
   (d) introducing, in response to the measured absorbance, caustic into the scrubber to maintain a concentration range of from about 5% to about 15%, wherein the caustic is introduced in response to the measured absorbance in accordance with a pre-determined set point value.

18. A polycarbonate production system configured to perform the process of claim 17.

19. A caustic scrubber comprising a near-infrared spectroscopy probe coupled thereto, further comprising a means to introduce caustic into the scrubber, wherein the caustic is introduced in response to the measured absorbance in accordance with a pre-determined set point value, and wherein the caustic is present in the scrubber within a concentration range of from about 5% to about 15%.

20. The scrubber of claim 19, wherein the probe is coupled to the scrubber via direct contact.

21. The scrubber of claim 19, wherein the probe is coupled to the scrubber via fiber optic.

22. The scrubber of claim 19, wherein the caustic scrubber is part of a polycarbonate production system.

23. The scrubber of claim 19, wherein the concentration range is from about 6% to about 8%.

24. The scrubber of claim 19, wherein the caustic is introduced in response to the measured absorbance to maintain the concentration range.

25. The scrubber as in any of claim 19 or 24, wherein the caustic is introduced automatically into the scrubber.

26. The scrubber of claim 25, wherein the automatic introduction of caustic is in accordance with a pre-programmed algorithm.

27. A polycarbonate production system comprising the caustic scrubber of claim 19.

28. A polycarbonate production system comprising the caustic scrubber of claim 19 and configured to perform the process of claim 1.

29. The process 19, wherein the scrubber is part of a polycarbonate production system.

30. A caustic control system in a polycarbonate production system, the scrubber comprising:
   (a) a caustic scrubber;
   (b) a spectroscopy probe coupled to the scrubber via fiber optic, wherein the probe is capable of measuring the near-infrared absorbance in the scrubber;
   (c) means for determining caustic concentration in the scrubber from the measured absorbance; and
   (d) means to automatically introduce caustic into the scrubber to maintain a concentration range of from about 5% to about 15%, wherein the caustic is introduced in response to the measured absorbance in accordance with a pre-determined set point value.

31. A polycarbonate production system comprising the caustic control system of claim 30.

32. A polycarbonate production system comprising the caustic control system of claim 30 and configured to perform the process of claim 17.

* * * * *